(12) United States Patent
Lacoste et al.

(10) Patent No.: US 8,802,209 B2
(45) Date of Patent: Aug. 12, 2014

(54) MULTI-LAYERED PLASTIC POLYMERIC CONTAINER FOR THE STORAGE OF PHARMACEUTICAL COMPOSITIONS

(75) Inventors: Sandrine Lacoste, Carignan (FR); Laurence Peyrot, Les Billaux (FR); Eliane Boivin, Bordeaux (FR)

(73) Assignee: Ceva Santé Animale, Libourne (FR)

( * ) Notice: Subject to any disclaimer, the term of this patent is extended or adjusted under 35 U.S.C. 154(b) by 571 days.

(21) Appl. No.: 12/663,972

(22) PCT Filed: Jun. 12, 2008

(86) PCT No.: PCT/EP2008/057442
§ 371 (c)(1),
(2), (4) Date: Dec. 10, 2009

(87) PCT Pub. No.: WO2008/152122
PCT Pub. Date: Dec. 18, 2008

(65) Prior Publication Data
US 2010/0176136 A1    Jul. 15, 2010

Related U.S. Application Data

(60) Provisional application No. 60/952,953, filed on Jul. 31, 2007.

(30) Foreign Application Priority Data

Jun. 15, 2007  (FR) ...................... 07 04259

(51) Int. Cl.
*B32B 1/02* (2006.01)
(52) U.S. Cl.
USPC ........................ 428/36.7; 428/35.7

(58) Field of Classification Search
USPC ............... 428/34.1, 35.2–35.4, 35.7–36.2, 428/36.5–36.91
See application file for complete search history.

(56) References Cited

U.S. PATENT DOCUMENTS

| | | | |
|---|---|---|---|
| 4,079,850 A | 3/1978 | Suzuki et al. | |
| 4,198,327 A | 4/1980 | Matsumoto et al. | |
| 4,281,045 A | 7/1981 | Sumi et al. | |
| 4,370,368 A | 1/1983 | Hirata et al. | |
| 4,451,512 A | 5/1984 | Yazaki et al. | |
| 4,472,555 A * | 9/1984 | Schmukler et al. | 525/74 |
| 4,705,708 A | 11/1987 | Briggs et al. | |
| 4,929,482 A | 5/1990 | Moritani et al. | |
| 5,164,258 A | 11/1992 | Shida et al. | |

(Continued)

FOREIGN PATENT DOCUMENTS

| | | |
|---|---|---|
| EP | 0258990 | 3/1988 |
| EP | 0288595 | 11/1988 |
| EP | 0398734 | 5/1989 |
| GB | 2006108 | 5/1979 |

(Continued)

*Primary Examiner* — Walter B Aughenbaugh
(74) *Attorney, Agent, or Firm* — Wolf, Greenfield & Sacks, P.C.

(57) ABSTRACT

Multi-layered plastic polymeric container useful for the storage and conservation of pharmaceutical compositions, sterile or non sterile, which comprises an inner layer and an outer layer, a gas barrier layer, and adhesive layers.

20 Claims, 8 Drawing Sheets

100 ml     250 ml     500 ml

(56) References Cited

U.S. PATENT DOCUMENTS

| | | | |
|---|---|---|---|
| 5,202,192 A | 4/1993 | Hope et al. | |
| 6,037,063 A | 3/2000 | Muschiatti et al. | |
| 6,191,241 B1 * | 2/2001 | Starzewski et al. | 526/161 |
| 6,599,639 B2 * | 7/2003 | Dayrit et al. | 428/475.8 |
| 6,677,013 B1 | 1/2004 | Curie et al. | |
| 2004/0005475 A1 | 1/2004 | Curie et al. | |
| 2006/0251838 A1 | 11/2006 | Inoue et al. | |

FOREIGN PATENT DOCUMENTS

| | | |
|---|---|---|
| JP | 57116618 | 7/1982 |
| JP | 2001088817 | 4/2001 |
| JP | 2003267431 | 9/2003 |
| JP | 2004202876 | 7/2004 |
| WO | WO 90/14395 | 5/1989 |
| WO | WO 00/63085 | 4/1999 |

* cited by examiner

MULTI-LAYERED PLASTIC POLYMERIC CONTAINER FOR THE STORAGE OF PHARMACEUTICAL COMPOSITIONS

This application is the National Stage of Int'l App'l No. PCT/EP2008/057442, filed Jun. 12, 2008, which claims benefit of U.S. Ser. No. 60/952,953, filed Jul. 31, 2007 and claims priority of French App'l No. 07/04259, filed Jun. 15, 2007. The entire contents and disclosures of the preceding applications are incorporated by reference into this application.

The present invention relates to a multi-layered plastic polymeric container for storing compositions, particularly pharmaceutical compositions, which may be sterilized by irradiation with or without the composition and allows for a stable conservation of said composition for a long period of time in sterile conditions. Also, the container of the present invention fulfils the strict regulations and requirements for storing pharmaceutical compositions.

Some pharmaceutical compositions, such as injectable compositions, require to be sterilized before administration. These pharmaceutical compositions are thus in general manufactured and stored in sterile conditions. The container may be sterilized either empty or filled with a composition. Alternatively, the container and the composition may be sterilized separately, and the container may then be filled in sterile conditions according to well known methods in the art.

The container, and particularly its inner layer which is in direct contact with the pharmaceutical composition, generally have a definite structure as required by European Pharmacopeia regulations. The container also must maintain properties of resistance after sterilization, as well as stability, mechanical resistance, transparency, and impermeability towards environmental factors, chemical products or various treatments; the reference being the glass material.

The material for the packaging or container must be pharmaceutically acceptable and should therefore not alter the quality of the pharmaceutical compositions. Also, pharmaceutical compositions must not alter the nature and composition of the container or packaging in contact therewith. Such alterations may result in the migration of chemicals from and to the packaging or container and the pharmaceutical composition. Such chemicals may be impurities, degradation products that appear over time under the action of oxygen, light and temperature, or due to processing of the container or packaging, such as sterilization process by irradiation. These interactions may alter over time the chemical properties of the pharmaceutical composition, such as the stability of the active ingredient and/or of the container or packaging, transparency and/or colour of the composition or flask, thereby reducing the lifetime of the container or packaging. Furthermore, such interactions may modify the sterility, safety and efficacy of the pharmaceutical composition.

Containers or packagings that are made of plastic materials have been broadly developed as containers of pharmaceutical compositions. Materials such as polyolefins (polypropylene (PP), polyethylene (PE) poly(ethylene terephtalate) (PET), poly(vinyl chloride) (PVC), poly(ethylene-vinyl acetate) have been used for manufacturing monolayer containers such as pockets of perfusion, syringes, pipes. These materials are also used for syrups containers, tablets containers, or sterile aqueous solutions containers, particularly physiological serum and ophthalmic compositions. However, the use of these materials in the manufacture of monolayer containers for compositions that are sensitive to environmental factors are not generally satisfying, since the monolayer is not sufficient as a barrier to store in stable conditions the pharmaceutical composition over time, and the composition is sensitive to treatments of the container such as sterilization or solvent actions.

Complex multi-layered containers have also been developed for use inter alia for packaging of foods and cosmetics. Such packagings or containers are in general formed by the association of several material layers (sheets), thereby improving the properties of the packagings, which is then particularly less rigid, less breakable, and more resistant to heat, to light, to gas and chemical treatments.

These multi-layered containers are made of materials such as polyamides, polyolefin (PO) (polypropylene (PP), polyethylene (PE)), polyethylene terephtalate (PET), polyvinyl chloride (PVC), poly(ethylenevinyl acetate) which are associated with gas barrier layer made of ethylene vinyl acetate copolymer (copolymer EVOH), ethyl vinyl acetate (EVA), and polyamides, in order to yield an increased barrier protection against oxygen and water vapor and limit any possible alterations of the pharmaceutical composition.

For example, the European application EP0288595 describes multi-layered layer containers having from the inside to the outside, a thick layer of polypropylene, a gas barrier layer formed of copolymer EVOH), bound to a layer of polypropylene by an adhesive, and an external layer made of polyamide.

Other multi-layered containers are described in U.S. Pat. No. 4,919,984 and comprise a central gas barrier layer formed of copolymer EVOH, inner and outer layers that are made of a thermoplastic resin which is capable of resisting to humidity, and intermediary resin layers in between the outer and inner layers, made of polyacrylic polymers, cellulose, and divinylbenzene that are marketed under AQUAKEEP® or SUMIKAGEL®, and present high capacity of water absorption.

Furthermore, U.S. Pat. No. 5,164,258 describes a multi-layered container comprising a central gas barrier layer formed of EVOH, outer and inner layers made of a mixture of polyolefins and agents capable of increasing water vapour transmission rate, thereby avoiding altering of the properties of the central gas barrier layer.

These various multi-layered containers are thus restricted to moist heat sterilisation (autoclaving), but may not be used when sterilization of the container, empty or filled, is conducted using beta or gamma irradiation; these methods of sterilization by irradiation being preferred for sterilizing non aqueous compositions. Also, gamma irradiation is particularly preferred since gamma rays penetrate more deeply in the structures than beta rays, thereby allowing sterilizing of a greater number of containers or bottles at the same time, the bottles being filled or empty. This step of sterilization may however induce modifications of the containers properties, which may become more breakable. Gamma rays generally alter the polyolefins, and for example break the polypropylene chains. Further, gamma rays sterilization is subject to regulations ISO11137 which require consideration of several parameters, such as size of the product to sterilize or the use of additives. Also, the regulations ISO11137 require the use of maximal irradiation dose. Particularly, in the case of polyolefins containers, such as polypropylene containers, the irradiation dose must be lesser than 60 kGy (Kilo Gray).

Containers that have been developed so far are not adapted to the constraints of sterilization by irradiation and present many alterations of the polymers of the containers after irradiation. Also, such containers are not useful for long term storage of sterile compositions which are found to be altered by environmental factors. In addition, compatibility of these containers with pharmaceutical compositions is usually poor.

The present invention provides multi-layered containers that overcome defects of the above-described containers. The containers of the present invention allows for the storage of liquid or non liquid, sterile pharmaceutical compositions comprising solvents aqueous or non aqueous.

The present invention thus relates to a plastic multi-layered polymeric container for the storage of sterile compositions, comprising at least three layers of different types, i.e., a polymer layer, a gas barrier layer and an adhesive layer. Preferably, the container comprises five or six layers, including inner and outer layers of polyolefin polymer or polyester in direct contact with the composition and in contact with the environment, respectively, a central gas barrier layer and two intermediate adhesive layers, each of which provides adhesion of the polymer layer with the central gas barrier layer.

Advantageously, the invention relates to a plastic multi-layered stable container which may be sterilized by irradiation when filled with a pharmaceutical composition or empty. Also, the present invention relates to a plastic multi-layered stable container being sterile. Finally, the present invention relates to a plastic multi-layered polymeric stable container which can be sterilized by irradiation, either empty or filled with a sterile or non sterile composition. Plastic multi-layered polymeric stable containers of the present invention are preferably sterilized by gamma irradiation.

It has been found that association of at least two outer and inner layers comprising particular polymers, with at least one gas barrier central layer results in a significant reduction of the alteration and degradation of the polymers after sterilization by irradiation. Such association is thus useful for conditioning pharmaceutical composition, for example sterile compositions, that may then be stored with optimal stability, and stay chemically inert over time, as well as optimal resistance of the container.

Containers of the present invention may contain aqueous or non aqueous compositions, or solid compositions, such as powders, tablets, pills, capsules, granules, pellets, pastes, or gels.

Liquid non aqueous compositions generally contain, in addition to the active ingredients, vegetal oils, and aggressive organic solvents, e.g., heterocyclic organic solvents, such as acetamides and pyrrolidone, oil solvents, such as glycol ester or propylene glycol diester, or glycerides, such as triglycerides. Vegetal oils usually migrate within the polyolefin layers, causing the layer to swell. This reaction is due to the high affinity of polyolefins for the vegetal oils of the composition. Similarly to the vegetal oils, but to a lesser extend, the organic solvents also react with the polyolefins chains. However, according to the present invention, migration of the components of the non aqueous solvents within the polyolefin compositions has not been observed.

The polymer layer is preferably made of polyolefins and polyesters. Preferred polymers are polyolefins, such as polypropylene or polyethylene, either homopolymers or copolymers. Polyolefins are formed of unsaturated hydrocarbonated monomers having the following general formula R=$CR_1R_2$ (wherein $R_1$ and $R_2$ are —H, —$CH_3$, or —$CH_2$—$CH(CH_3)_2$). Most preferably, outer and inner layers comprise polypropylene copolymer. Polypropylene (PP) has the following chemical formula: —$(CH_2$—CH—$CH_3)_n$— and is obtained by polymerization of propylene monomers ($CH_2$=CH—$CH_3$) in presence of catalysers according to the Ziegler-Natta reaction. Polypropylene is a statistical copolymer of propylene/ethylene with a Melt Flow Rate (MFR) ranging from 1 to 15 g/10 min, and preferably about 2 g/10 min (ISO 1133), a fusion temperature ranging from 130 to 170° C., and a density from 0.9 to 1.0 g/cm³. Polypropylene is initially under the form of beads which are extruded for the manufacture of the layer.

According to the present invention, the inner layer of the container preferably comprises polypropylene while the outer layer comprises a mixture of polyolefin and at least one branched polyolefin. Branched polyolefins present a base linear structure on which are coupled or bound a plurality of polyolefins polymeric arms. Branched polyolefins as used in the present invention comprise arms or ramifications of polymers comprising 1-alcene having 3 to 30 carbon atoms, preferably between 5 and 15 carbon atoms, and most preferably 8 carbon atoms, such as polyoctenes. They are used in a proportion comprised between 5 and 25%, between 10 and 25%, and preferably between 15 and 25%, and most preferably in proportion of about 20% within the outer layer. Preferably, the outer layer comprises a combination of polypropylene and 20% polyoctene.

Also, according to the present invention, outer and inner layers comprise at least one and preferably up to three conventional additives within combination with basic polymers. The conventional additives may be chosen among antioxidants, plasticizers, stabilizers, lubricants, colorants, mechanical strengtheners.

Preferably, the outer and inner layers comprise antioxidants as authorized by the European Pharmacopeia, such as butylhydroxytoluene; ethylene bis(3,3-bis(3(1,1-dimethylethyl)-4-hydroxy-phenyl) butanoate); pentaerythrityl tetrakis (3-(3,5-di-tert-butyl-4-hydroxyphenyl)-propionate) or IRGANOX 1010®, 4,4',4"-(2,4,6 trimethylbenzene-1,3,5-tri-yltrismethylene)-tris(2,6-bis(1,1-dimethyl-ethyl)phenol) also designated IRGANOX 1330®; octadecyle 3-(3,5-di-tert-butyl-4-hydroxyphenyl)propionate or IRGANOX 1076®; phosphite tris(2,4-bis(1,1-dim ethylethyl)-phenyl) or IRGAPHOS 168®; 1,3,5-tris(3,5-di-tert-butyl-4-hydroxy-benzyl)-s-triazine-2,4,6(1H,3H,5H)-trione or IRGANOX 3114®; 2,2'-bis(octadecyloxy)-5,5'-spirobi(1,3,2-dioxaphosphinane); dioctadecyle disulfide, didodecyl 3,3'-thiodipropanoate; dioctadecyle 3,3'-thiodipropanoate; or a mixture of seven components that are obtained from the reaction of di-tert-butyl phosphite with trichloride biphosphorus, with biphenyle and 2,4-bis(1,1-dimethylethyl)phenol; copolymer of dimethyl succinate and of (4-hydroxy-2,2,6,6-tetramethylpiperidin-1-yl)ethanol, or a mixture of at least two of these additives.

Preferably, the outer and inner layers of polymer according to the present invention comprise a combination of up to three additives which may be either primary phenol additives or secondary phenol antioxidants. Most preferred secondary phenol antioxidant is IRGAPHOS 168® and preferred primary phenol antioxidants are chosen among IRGANOX 1010®, IRGANOX 1330® and/or IRGANOX 3114®. Also, inner and outer layers comprise a combination of up to three additives chosen among the four that are described above. Phenol antioxidants such as IRGAPHOS 168®, IRGANOX 1010® and IRGANOX 3114® are present in proportions from about 0.001% to 0.01%. Maximal amount of antioxidant additives within the outer and inner layers is generally less than 0.3%, except for the butylhydroxytoluene and the mixture of the seven components which correspond to the reaction products of di-tert-butyl phosphite with trichloride biphosphorus, and with biphenyl and 2,4-bis(1,1-dimethylethyl)phenol, which may be present within the maximal amount of 0.125 and 0.1%, respectively.

Compounds such as ethylene vinyl alcohol (EVOH) or polyamide (PA) are preferred as gas barrier agent of the central layer. Most preferably, the gas barrier agent is EVOH.

The EVOH contains from 20% to 60% of ethylene, preferably from 27% to 47%, more preferably of about 32%. The EVOH has a fluid index of 1 to 5 g/10 min, preferably of about 1.6 g/10 min, a density of 1.19 g/cm$^3$, a Tm (temperature of fusion) of 183° C., a Tg (temperature of vitreous transition) of 69° C., a OTR (Oxygen Transmission Rate), also called QO$_2$ for <<Oxygen Gas Permeation>> or PO$_2$ for <<Oxygen Permeability>>) of 0.4 ml 20 µm/m$^2$·day·atm. The oxygen transmission rate is equal to 1.5 ml/m$^2$/24 h for a 20 µm thick film at 20° C., 85% HR (relative humidity).

The adhesive agent layer may be formed of modified polyolefins grafted with variable functional groups depending on the composition of the outer and inner layers. The functional groups may be polyolefins, polyamides, or polycarbonates, and allow binding between the polyolefins and EVOH. Preferably, polyolefins are modified by functional groups such as homopolymers with propylene. The functional groups may be adapted to the various polymers ranging from polyolefins to PET and polystyrene. Most preferably, the adhesive agent used belongs to the ADMER® compounds, which is marketed by company Mitsui Chemical, such as for example ADMER QB 501 E®.

Incorporation of an adhesive agent ensures perfect adhesion between both layers of polyolefin and copolymer EVOH. Absence of adhesive may alter the multi-layered structure, and polyolefin layers may loose their transparency. The structure of adhesive agents being close to polyolefins or copolymers, maintains characteristics of each of these polymers.

Outer and inner layers based on polymer polypropylene are devoid of agents which act by increasing the water vapour transmission rate.

Multi-layered polymeric plastic containers according to the present invention are sterilized, with or without their content, by beta or gamma irradiation. According to a preferred embodiment, gamma irradiation is used, and containers so sterilized maintain a stable structure even after gamma irradiation as demonstrated by drop test and tensile strength studies in the Examples below. When antioxidant additives are incorporated in the outer and inner layers of the containers according to the present invention, these antioxidants are not detected after irradiation.

Therefore, according to a preferred embodiment, the multi-layered plastic polymeric container is sterilized by irradiation and contains inner and outer layers in direct contact with the composition and the environment, respectively, the outer layer comprising a mixture of polyolefins or polyesters and at least one branched polyolefin, which is present in the range from about 5 to 25%, or from 10 to 25%, from about 15 to 25%, and preferably in a proportion of about 20%, the inner layer comprising a mixture polymers polyolefins or polyesters, a gas barrier layer, and two intermediary adhesive layers in between the central layer and the inner and outer polymeric layers.

Outer and inner layers may be made of polyolefins, such as for example, polypropylene and/or polyethylene under the form of homopolymers or copolymers. The outer layer comprises polypropylene and/or polyethylene in a proportion ranging from 5-25%, 10-25%, or 15-25% and preferably of about 20%, at least a branched polyolefin such as polyalcene having 3 to 30 carbons, preferably 5 to 15 carbons. Preferably, branched polyolefins used in the outer layer are chosen among polyoctene, polybutene, or polyhexene in a proportion of about 20%. Most preferably, polyoctene is used in a proportion of about 20%. Polyoctenes are marketed under EXACT 0201®, EXACT 0202®, EXACT 0203®, EXACT 801® by Dex-Plastomers or Exxon. The polybutenes and polyhexenes are marketed under EXACT3035® and EXACT9106® by Dex-Plastomers or Exxon. The gas barrier layer comprises compounds such as ethylene vinyl alcohol (EVOH) or polyamide (PA). Preferably EVOH comprises from 20% to 60% of ethylene arms, or from 27% to 47%, and most preferably a proportion of 32% of ethylene arms. Also, adhesive layer comprises compounds of the polyolefin family such polyolefin are grafted with functional groups chosen among polyolefin, polyamide, or polycarbonate.

The outer and inner layers also comprise up to three additives, such as antioxidants, plasticizers, stabilizers, lubricants, colorants, and mechanical strengtheners. The antioxidants are as described above and are present in proportion of less than 0.3% within outer and inner layers. More preferably, these include IRGANOX 1010®, IRGAPHOS 168®, and IRGANOS 3114®.

The outer layers may also comprise additives allowing softening the outer layer of polypropylene of the multi-layered plastic polymeric containers. Alternatively, the additives may render the outer layers more resistant to the sterilization by irradiation. Such additives may be inter alia polymers SEBS, i.e., polypropylene polymers marketed under the name of CAWITON PR 3704° by the company Wittenburg, or polypropylene marketed under the name PURELL® by Basell, or polyolefins marketed under the name MELIFLEX® by the company Melitek.

Therefore, according to a preferred embodiment, non-sterile multi-layered containers before irradiation comprise:

an outer layer 1 comprising a mixture of polypropylene and polyoctene in a proportion ranging from 5 and 25%, 10 and 25%, or 15 and 25%, and preferably equal to about 20%;

a first intermediate outer layer 2 comprising an adhesive agent of the type ADMER® in a sufficient amount;

a central layer 3 comprising EVOH in a sufficient amount;

a second intermediate inner layer 4 comprising an adhesive agent of the type ADMER® in a sufficient amount; and an inner layer 5 comprising polypropylene.

According to a preferred embodiment, the multi-layered plastic polymeric container is non sterile before irradiation and comprises:

an outer layer 1 comprising polypropylene, about 20% of polyoctene, and up to three additives chosen among antioxidants, plasticizers, stabilizers, lubricants, colorants, and mechanical strengtheners;

a first intermediate outer layer 2 comprising an adhesive agent of the type ADMER® in a sufficient amount;

a central layer 3 comprising EVOH in a sufficient amount;

a second intermediate inner layer 4 comprising an adhesive agent of the type ADMER® in a sufficient amount; and an inner layer 5 comprising polypropylene, and up to three additives chosen among antioxidants, plasticizers, stabilizers, lubricants, colorants, and mechanical strengtheners.

According to another preferred embodiment, the multi-layered plastic polymeric container is non sterile before irradiation and comprises:

an inner layer 1 comprising polypropylene, about 20% of polyoctene, and up to three antioxidants chosen among IRGANOX 1010®, IRGAPHOS 168®, and IRGANOX 3114®;

a first intermediate layer 2 comprising an adhesive agent of the type ADMER® in a sufficient amount;

a central layer 3 comprising EVOH in a sufficient amount;

a second intermediate layer 4 comprising an adhesive agent of the type ADMER® in a sufficient amount; and an inner layer 5 comprising polypropylene and up to three antioxidants chosen among IRGANOX 1010®, IRGAPHOS 168®, and IRGANOX 3114®.

According to this embodiment, the container comprises five layers and presents an average total thickness ranging from 380 to 1320 μm:

an outer layer 1 which is in contact with the environment, is made of polymers polyolefins and/or polyesters, and has an average thickness ranging from 150 to 400 μm, preferably from 150 to 300 μm, and most preferably of about 250 μm;

an intermediate outer layer 2 of adhesive agent, which presents an average thickness from 5 to 75 μm, preferably from 5 to 50 μm, and most preferably of about 10 μm;

a central layer 3 of gas barrier copolymers, which presents an average thickness from 20 to 170 μm, preferably 20 to 100 μm, and most preferably about of 30 μm;

an intermediate inner layer 4 of adhesive agent, which presents an average thickness ranging from 5 to 75 μm, preferably 5 and 50 μm, and most preferably about 10 μm;

an inner layer 5, in contact with the composition, made of polyolefins or polyesters, which presents an average thickness ranging from 200 to 600 μm, preferably 450 to 600 μm, and most preferably of about 500 μm.

According to this embodiment, the multi-layered plastic polymeric sterile containers after irradiation are similar to the non-irradiated containers, with the exception of antioxidants which are not detectable within the outer and inner layers of the containers after irradiation.

The sterile plastic multi-layered polymeric containers after irradiation thus preferably comprise:

an outer layer 1 comprising a mixture of polypropylene and polyoctene in a proportion from 5-25%, 10-25%, or 15-25% and about 20%;

a first intermediate outer layer 2 comprising an adhesive agent such as ADMER® in a sufficient amount;

a central layer 3 comprising EVOH in a sufficient amount;

a second intermediate inner layer 4 comprising an adhesive agent such as ADMER® in a sufficient amount; and an inner layer 5 comprising polypropylene.

The average thickness of sterile containers is similar to that of the containers before irradiation.

According to another embodiment, the multi-layered plastic polymeric container of the present invention may comprise six layers. The container has the same structure as that of a five-layer container with an inner polymeric layer in direct contact with the composition and the outer polymeric layer in direct contact with the environment, and presents an additional polymeric layer. Such additional polymeric layer is useful when additional compounds, such as colorants are used so as to provide visual characteristics to the container. These additional compounds may thus be introduced within the additional polymeric layer which has no direct contact with the composition and environment. This absence of direct contact between the additional polymeric layer and the composition or the environment is necessary to prevent any interaction between the composition and said additional compounds, and to prevent degradation of said additional compounds under the action of the environment (air, humidity, etc.).

According to another object, the present invention relates to the multi-layered plastic polymeric container comprising a liquid aqueous or non aqueous composition or alternatively comprising a solid composition such as powders, tablets, pills, capsules, granules, pellets, pastes, or gels.

The container is useful for storage of compositions in sterile conditions. The container may be first filled with the composition and sterilized by irradiation together with the composition, and particularly by gamma or beta irradiation. Alternatively, the composition and the container may be sterilized separately, and the container is then filled with the sterile composition under sterile conditions. Sterilization of the composition may be conducted by conventional methods, such as filtration, by moist or dry heat or by irradiation, whereas container is sterilized by gamma or beta irradiation.

The multi-layered plastic polymeric container, according to the present invention, is sterilized by irradiation at dose rates ranging from 10 kGy to 25 kGy, and is then filled with the composition under sterile conditions, the compositions being filtrated for example on a filter 0.22 μm, prior to the filling.

Preferably, containers that are either empty or filled with the compositions are sterilized with gamma irradiation and maintain a good stability over time as demonstrated by the Examples herein below. Gamma rays have a high penetration into the structures, thereby allowing to sterilization of a greater number of containers empty and/or filled in a very efficient manner.

Thus, multi-layered plastic polymeric containers according to the present invention allow for an efficient storage of sterile compositions as that of glass containers. As demonstrated in the Examples, said multi-layered containers allow the conservation of physical and chemical properties of the containers and compositions over time after sterilization by irradiation.

When sterile compositions are stored in the containers of the present invention, organoleptic characteristics as well as the physical and chemical properties are maintained over time similar to that of the glass container. Conservation of the composition in plastic containers is said to be relative to the glass container, when evolution of the properties in plastic containers is compared to the evolution of the same parameters for an identical composition in a glass container. Storage of the composition in the multi-layered plastic polymeric container may also be appreciated in an absolute manner. Parameters are then measured and are not compared to those of a composition in a glass container. The evaluation of the conservation of the composition in an absolute manner is required in the case of pharmaceutical or veterinary compositions. Regulations and Pharmacopoeias (European Pharmacopeia) define parameters that have to be taken into consideration and in what extend these parameters may vary in an acceptable manner. The evolution over time of these parameters allows assessing chemical and physical stability of the pharmaceutical compositions over time.

In order to assess conservation of the pharmaceutical composition, several qualitative and quantitative parameters may be taken into account. Qualitative parameters include colour, transparency, and smell of the composition. Quantitative parameters of stability of the composition over time include concentration of the active ingredient in the composition, and relative percentage of degradation products in comparison with the active ingredient, pH, and viscosity.

Variations of these parameters are function of the composition, i.e., solution, suspension, or emulsion, of the nature of the active ingredient, of the route of administration of the composition, i.e., injectable, oral, or topic. Visual evaluation of the composition and determination of the concentration of the active ingredient in the composition, percentage of the degradation products relative to the active ingredient and eventually the pH for the multi-layered plastic polymeric container filled with the composition may be compared to same parameters for the glass container filled with the same composition.

A pharmaceutical composition is said to be stable when the concentration of active ingredient in the composition, the percentage relative of degradation products, and optionally the pH, vary within proportions such that efficacy and safety of the composition are not modified. These proportions are also function of the nature of the active ingredient, the form of the composition, and the mode of administration. For example, appearance of degradation products should be as low as possible for injectable compositions contrary to topical compositions. These various parameters are generally provided in the pharmaceutical regulations, particularly European Pharmacopeia, and such parameters are measured according to pre-defined methods. The measures are conducted at various times, i.e., 3 months, 6 months, 12 months, 18 months, and 24 months, at various temperatures, i.e., 4° C., 25° C. or 40° C., and under defined humidity conditions.

For example, the pharmaceutical composition is considered to be stable when the above parameters, after 6 months storage at a temperature of 40° C. and under relative humidity of 75%, vary in specified proportions as detailed below. Said composition does not present any significant changes of aspect, i.e., colour, transparency and odour. Acceptable variations of the concentration of the active ingredient in the composition are generally less than 10%, and preferably less than 5%. Acceptable variations of the relative percentage of the degradation products as compared to the active ingredient are generally less than 10%, and preferably less than 5%. Acceptable pH variations are generally not more than 0.5.

Duration of the storage may last as long as stability of composition during storage is maintained and as long as the variations of the concentration of the active ingredient and apparition of degradation products are low over time.

Active ingredients of these compositions generally comprise therapeutic and pharmaceutical agents, prophylactic agents, diagnostic agents, and any other agents that are capable of treating, preventing or diagnosing a pathology, an infection, or any other diseases of human or animal non human subjects, such as mammals, fishes, birds, insects and any other organisms, and even plants. Active ingredients may be for example antibiotics, such as amoxicillins, cetfiofur, oxytetracyclines, trimethoprimes, clarithromycins, in solution or suspension, anti-infective agents, vaccines, vitamins, non-steroid anti-inflammatory agents such as meloxicam, indomethacin and zileuton, anti-depressive agents, such as imipramine, anthelminthic agents such as praziquantel, pyrantel and ivermectine, anti-viral agents, cardiotonic agents such as digoxin, antihypertensive agents, diuretic agents such as furosemide, therapeutic agents for the treatment of CHF (cardiac heart failure), enzymes, antagonists inhibitors, diagnostic agents for the diagnosis of cardio-vascular diseases, metabolism dysregulation or of atherosclerosis, G protein coupled receptors (GPCR), kinases and proteases, or agents for the diagnosis of infectious diseases. Also, diagnostic agents may be polypeptides, nucleic acids, polysaccharides, lipids, glycoproteins, glycolipids, carbohydrates, or small molecules. According to one aspect, diagnostic agents are markers of some tissues and may be radioisotopes and radioactive agents, or may be magnetic markers, fluorescent or chemoluminescent markers, or enzymatic markers, such as peroxidase, luciferase, beta-galactosidase, alkaline phosphatase, glucose oxidase or catalase. These diagnostic agents may also be antibodies, antibody fragments, peptides or proteins of a pathogenic organism, such as a cholera protein, hepatitis virus protein, influenza virus protein, interferons, interleukins, cytokine, human growth hormone (hGH), antisense oligonucleotides, RNAi, siRNA, or shRNA.

According to a preferred embodiment, pharmaceutical compositions are anti-inflammatory compositions and comprise a suspension of micronised powder of meloxicam, dispersed in a physiological vehicle, and comprising 0.01 to 1% by weight of xanthan gum, 0.1 to 2% by weight of silicon oxide and 50 to 70% of polyols mixture.

According to another preferred embodiment, pharmaceutical compositions comprise a suspension Ceftiofur HCl 5% as a veterinary treatment.

According to another aspect, the present invention relates to a kit which comprises multi-layered plastic polymeric containers and the pharmaceutical compositions as previously described, as well as instructions on the mode of administration of the composition to a subject. Such pharmaceutical composition may be present under liquid, aqueous or non aqueous form, or under solid form, such as for example powders, tablets, pills, capsules, granules, pellets, pastes, or gels.

This composition may be administered via multiple routes such as oral, nasal or by injections for the treatment and prevention of pathologies of human or non human animal, i.e., dogs, cats, horses, and rodents.

According to a preferred embodiment, kits according to the present invention are useful for the vaccination of human or non human animal, i.e., mammals and/or birds. Kits according to this embodiment comprise one or more antigenic agents that are capable to increase the immune response against a pathogenic agent.

Also, anti-inflammatory and/or analgesic kits according to the present invention comprise a multi-layered polymeric plastic container as previously described and a micronized powder of meloxicam, dispersed in a physiologic medium, and 0.01 to 1% by weight of xanthan gum, 0.1 to 2% by weight of silicon oxide, and 50 to 70% of a polyols mixture, as well as instructions for the administration of the anti-inflammatory composition to the non human animal.

In addition, kits according to the present invention are useful for the diagnosis of pathology in a subject or patient comprising a multi-layered plastic polymeric container as previously described one or more diagnostic agents, as well as instructions for the administration and use of the diagnostic kit for the diagnosis of a specific disease in a patient.

According to another object, the present invention relates to a process of manufacture of the multi-layered plastic polymeric container. Manufacture of the container according to the invention is realized by methods that are well known in the art, and preferably by extrusion-blown molding.

For example, a container with five layers may be obtained by using a conventional device with four concentric channels to manufacture a preform which is then blown-molded. By way of example, manufacture of such container with four channels is summarized in Table 1.

TABLE 1

| Layers | 5-layer containers | 6-layer containers |
| --- | --- | --- |
| Outer 1 | Polyolefin (channel C) | Polyolefin (channel C) |
| Intermediate 2 | Adhesive (channel A) | Adhesive (channel A) |
| Central 3 | Gas barrier agent (channel B) | Gas barrier agent (channel B) |
| Intermediate 4 | Adhesive (channel A) | Adhesive (channel A) |
| Inner 5 | Polyolefin (channel D + C) | Polyolefin (channel D-) |
| Inner 6 | — | Polyolefin (channel C) |

The present invention will be better understood from the Examples herein below referring to the following Figures.

EXAMPLES

Example 1

Preparation of a 5-Layer Container

Figure 1:
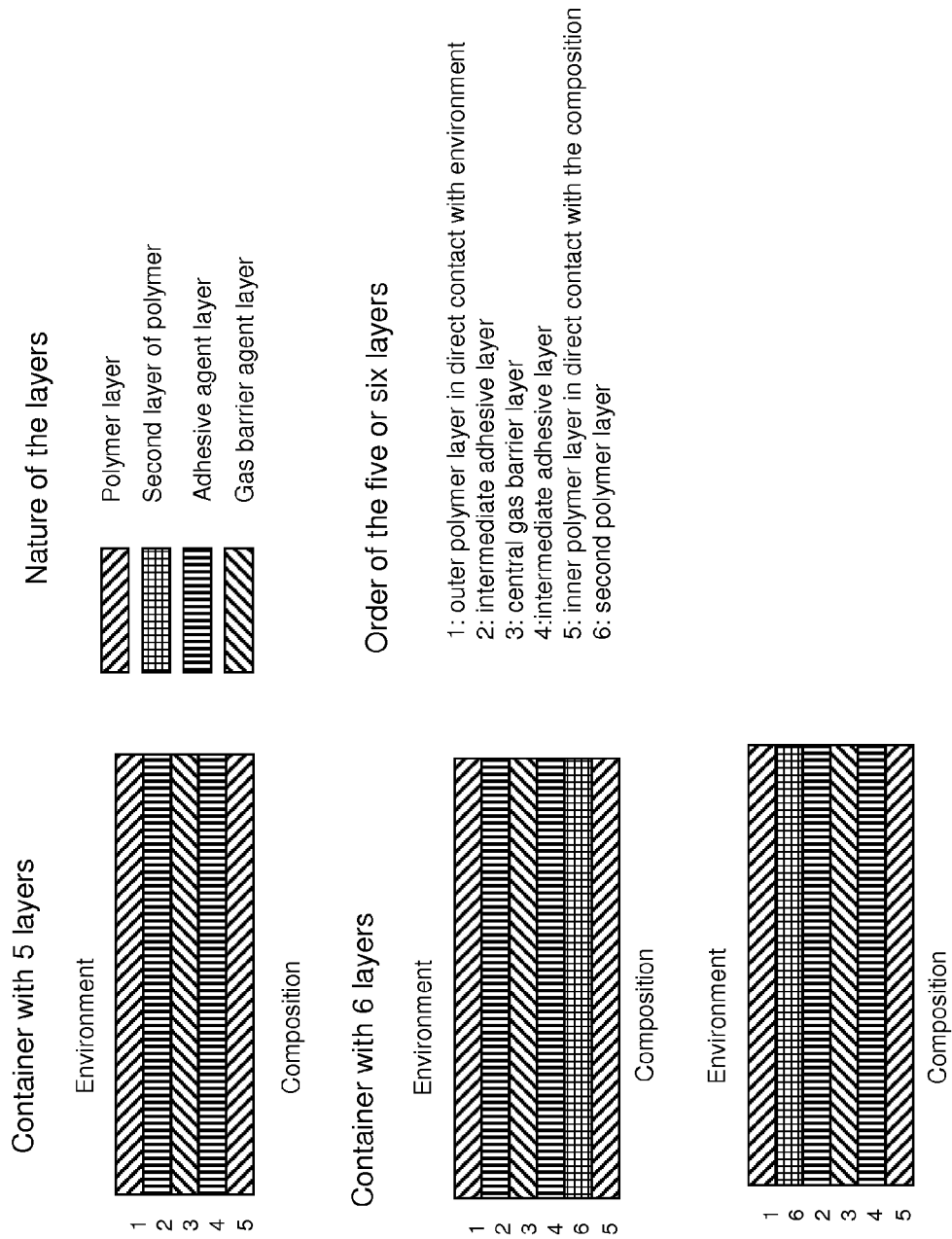
FIG. 1 displays a schematic transversal view of the wall of a container having five layers and of two containers having six layers. The layers are numbered as follows: 1/ outer layer of polymer in direct contact with the environment; 2/ intermediate adhesive layer; 3/ central gas barrier layer; 4/ intermediate adhesive layer; 5/ inner layer of polymer in direct contact with the composition; and 6/ a second polymer layer.
Figure 2:
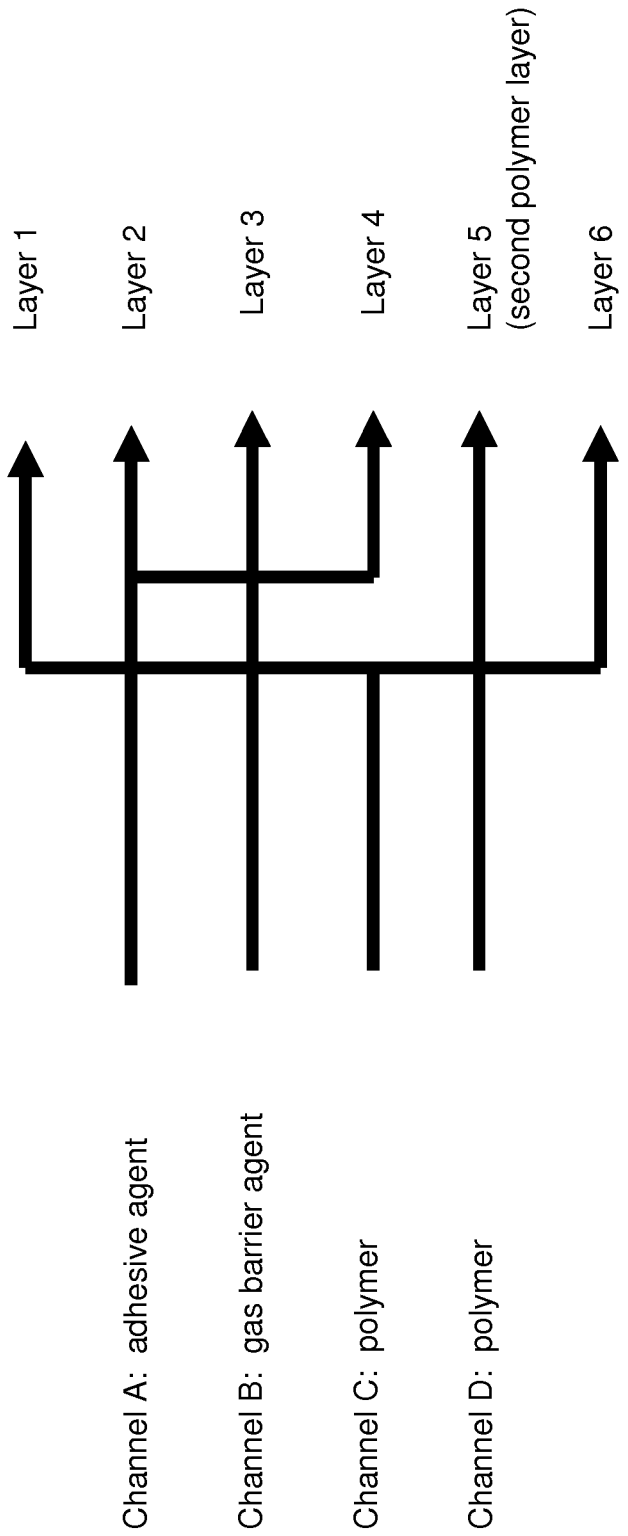
FIG. 2 shows a schematic view of the channels for the manufacture of the container according to the invention.

A container according to the invention, as obtained by extrusion-blown molding was manufactured and comprised 5 layers, as listed in the Table 2, under references 1 to 5, and with different channels (A to D) corresponding to the coextrusion of a preform that was expanded by blown molding for the manufacture of the bottle, as displayed in FIGS. 1 and 2.

TABLE 2

| Layers | Containers with 5 layers before irradiation | Container with 5 layers after irradiation |
| --- | --- | --- |
| Outer 1 | Polypropylene + 20% polyoctene + additives | Polypropylene + 20% polyoctene |
| Intermediate 2 | Adhesive | Adhesive |
| Central 3 | EVOH | EVOH |
| Intermediate 4 | Adhesive | Adhesive |
| Inner 5 | Polypropylene + additives | Polypropylene |

The container is sterilized using gamma irradiation of 25 kGy or 10 kGy and then filled under sterile conditions with a non aqueous composition that are beforehand filtered using a 0.22 μm filter.

Example 2

Characteristics of the Container and Resistance to Gamma Irradiation

Polypropylenes having a fluidity index of less than 8 associated with primary antioxidants such as IRGANOX® were used. A comparative study of the polypropylene primary material based container before and after irradiation at 25 kGy was conducted. This study was done (2A) to assess the physico-chemical properties by analysis of differential enthalpy (DSC) to study the structure of the materials, and (2B) to control the mechanical properties of the containers Example 2A Evaluation of the Physico-Chemical Properties by Analysis of Differential Enthalpy (DSC)

Thermodynamic characterization of the materials was provided by the differential enthalpy analysis, fusion temperature (Tf(° C.)) and enthalpy of fusion ($\Delta$Hf(J/g)). Crystalline regions of the materials were characterized by the fusion enthalpy parameters associated to the fusion temperature. Amorphous regions of the materials were characterized by the vitreous transition when the temperature was increased.

Variations of the thermodynamic parameters for materials that were sterilized by irradiation were usually observed for polyolefins. In effect, ionisant rays induced a modification of the temperature of fusion and enthalpy of fusion, indicating a modification of the semi-crystalline structure of polyolefins.

A physico-chemical study of the polypropylene of the outer layers of the multi-layered plastic polymeric container before and after irradiation at 25 kGy was conducted. Results were provided in Table 3.

A small variation of two parameters was detected. This small variation showed that the crystalline structure of the polypropylene was maintained. The analysis of differential enthalpy (DSC) was not statistically different between irradiated and non-irradiated bottles. In a surprising manner, these bottles were not subject to significant modifications of spectral or thermodynamic characteristics due to the irradiation treatment, thereby ensuring optimal conservation of the compositions.

TABLE 3

Analysis of differential enthalpy of the polypropylene of the outer layers of the bottle, before and after irradiation at 25 kGy.

| | Before irradiation | After irradiation 25 kGy |
| --- | --- | --- |
| Temperature of fusion (° C.) | 124.01 ± 0.53 | 126.36 ± 1.02 |
| Enthalpy of fusion (J/g) | 40.94 ± 2.84 | 41.19 ± 2.58 |

Example 2B

Evaluation of the Mechanical Properties of the Bottles

Extrusion-blown molding was used for manufacturing bottles having regular and layers having regular and homogeneous aspects. The irradiation step did not modify the structure of the layers.

A drop test was performed before and after irradiation in order to control the mechanical properties. The bottles filled with water were dropped vertically onto a solid base. A tensile strength test or axial strength test was also performed, wherein a vertical pressure of at least 55 kg is applied to the bottle. Finally, a cracking test was conducted and consisted in soaking the bottles for 70 h in a solution of tension-active at 50° C. and washing with water before controlling leakage thereof. Results of these experiments are provided in Table 4.

The mechanical properties of these bottles before and after irradiation at 10 kGy or 25 kGy were maintained. No cracking was observed, contrary to what was observed in the case of bottles made of polypropylene only.

The yellow coloration was very weak, the bottle remains mostly transparent, and the composition could be clearly seen through the bottles as it was usually required for injectable pharmaceutical compositions.

TABLE 4

Study of the mechanical properties of the bottles
before and after irradiation at 10 or 25 kGy

| Test | Non irradiated bottles | Irradiated bottles at 10 kGy | Irradiated bottles at 25 kGy |
|---|---|---|---|
| Droptest | Good | Good | Good |
| Axial strength | Good | Good | Good |
| Cracking test | Good | Good | Good |

Example 3

Compatibility Study of the Multi-Layered Plastic Polymeric Container

Interactions between composition and container have been assessed and showed that conservation of the composition in said containers is optimal over time and that there is no diffusion or migration of compounds of the composition towards materials of the container and that the integrity of the container and pharmaceutical composition is maintained.

At first, compatibility of the irradiated mono-, bi- and multi-layered irradiated bottles containing a sterile composition, such as non aqueous solution oxytetracyclin in a dimethylacetamide solvent was studied for a period of one month at 40° C., in comparison with a glass bottle. Aspects of the composition and of the container were observed.

Table 5 provides the results on the aspect of the composition and bottle prior to the storage ($T_0$) and after 1 month of storage at 40° C. under 75% relative humidity (RH).

Before storage, the composition was limpid with a light yellow color, and there was no modification of the aspect of the composition after a 1 month storage at 40° C. under 75% RH, thereby showing optimal conservation of the composition. In effect, interactions between the environment and the composition would have been evidenced by a composition turning to brown, also indicating the weakness of the bottle material as gas barrier, penetration of the oxygen and degradation of the active ingredient.

Similarly prior to storage bottles presented a transparent aspect, which was maintained after 1 month storage at 40° C. under 75% RH, and thus showed optimal stability of the bottles. On the contrary, migration of the elements of the composition or of the solvent within the bottle's material would have yielded an opaque aspect of the bottle. In effect, this migration would have induced a degradation of the polymer structure, thereby modifying the properties of the bottle.

These experiments showed that mono- and bi-layered bottles could not be used for storing compositions, whereas multi-layered polymeric bottles according to the present invention provide for optimal conservation.

TABLE 5

Compatibility study for mono-, bi- or multi-layered bottles

| Tested materials | Aspect of the material | Aspect of the composition |
|---|---|---|
| Glass | Transparent | Light yellow |
| PET* | Opaque | Light yellow |
| PET/PEN** | Opaque | Light yellow |
| COC*** | Transparent | Dark brown |
| PP | Transparent | Dark brown |
| PE | Transparent | Dark brown |
| PP/polyamide | Transparent | Dark brown |
| PE/polyamide | Transparent | Dark brown |
| Polyamide/PE | Transparent | Dark brown |
| PE/EVOH | Transparent | Dark brown |
| PP/EVOH/PP | Transparent | Light yellow |

*(Polyethylene terephtalate)
**(Polyethylene Naphtalate)
***(Cyclic Olefin Copolymer)

Also, as listed below are some parameters showing stability of the pharmaceutical compositions for a time period of 6 months at 40° C., with reference of the glass material which was neutral and was optimal in terms of gas barrier protection:

concentration of the active ingredient concentration of the degradation product color of the composition (degradation of the composition was evidenced by an intense color) in the bottles after irradiation.

Tables 6 and 7 provide the results before storage ($T_0$) and after 6-month storage at 40° C. under 75% RH.

These experiments showed that the composition, regardless of its form (solution, suspension, etc.) was conserved in optimal conditions with high stability. Also, a very low content of degradation products has been found. The composition thus remained safe over time. Furthermore, these experiments evidenced that stability of the composition when stored in the containers of present invention was as good as that of glass containers.

TABLE 6

Stability of a non aqueous sterile solution

| Solutions | $T_0$ (glass and plastic) | 6 months at 40° C. (glass) | 6 months at 40° C. (Plastic) |
|---|---|---|---|
| Concentration of active ingredient (%) | 19.49% | 18.70% | 18.66% |
| Concentration of degradation products (%) | 1.2% | 2.6% | 3% |
| Color of the composition | Light yellow | Light yellow | Light yellow |
| pH | 8.70 | 8.90 | 8.80 |

Non aqueous solutions containing oxytetracyclin in dimethylacetamide as solvent have been tested for stability

TABLE 7

Stability of a non aqueous sterile suspension

| Suspensions | $T_0$ (glass and plastic) | 6 months at 40° C. (glass) | 6 months at 40° C. (Plastic) |
|---|---|---|---|
| Concentration of the active ingredient (%) | 14.28% | 13.59% | 14.04% |
| Concentration of the degradation products (%) | 0.9% | 2.1% | 2.8% |
| Color of the composition | White suspension | White suspension | White suspension |

Non aqueous suspensions containing amoxicillin and propylene glycol diester have been tested for stability.

Similar properties were obtained for 5-layer bottles as shown in FIG. 1, wherein the layers in the following order 1, 2, 3, 4, 6, 5 and for bottles comprising layers in the following order: 1, 6, 2, 3, 4, 5.

Example 4

Preparation of a Bottle with 5 Layers

A container as in the present invention, was obtained by extrusion-blown molding, and comprised 5 layers as listed in the following Table 8:

TABLE 8

Composition of a multi-layered plastic polymeric bottle

| Layers | 5-layer bottle before irradiation | 5-layer bottle after irradiation |
|---|---|---|
| Outer layer | Polypropylene with IRGANOX 1010 ® + IRGAPHOS 168 ® + IRGANOX 3114 ® + polyoctene (20%) | Polypropylene + polyoctene (20%) |
| Intermediate layer | Adhesive | Adhesive |
| Central layer | EVOH | EVOH |
| Intermediate layer | Adhesive | Adhesive |
| Inner layer | Polypropylene with IRGANOX 1010 ® + IRGAPHOS 168 ® + IRGANOX 3114 ® | Polypropylene |

Example 5

Characterization of Interactions Between the Multi-Layered Plastic Polymeric Container and the Active Ingredients of the Composition Analysis of differential enthalpy indicated the fusion temperature (Tf(° C.)) and enthalpy of fusion (ΔHf(J/g)), thereby allowing to thermodynamically characterize the materials. The enthalpy of fusion and fusion temperature characterized the crystalline regions of the materials. Vitreous transition characterized amorphous regions of the material.

Variations of the thermodynamic parameters for the radio-sterilized materials were generally evidenced for polyolefins. In effect, ionizing radiations induced a modification of the fusion temperature and fusion enthalpy, as well as a modification of the semi-crystalline structure of the polyolefins.

A physico-chemical study of the outer layers made of polypropylene before and after irradiation at 25 kGy was performed. Results were provided in the following Tables 9-11.

A very low variation of the two parameters was observed. This small variation showed that the crystalline structure of polypropylene was preserved. The DSC thus did not evidence any substantial difference between irradiated and non irradiated bottles. Surprisingly, these containers were not subject to any substantial modifications of their spectral and thermodynamic characteristics due to the irradiation treatment. Conservation of the compositions was thus optimal.

TABLE 9

Analysis of additives in the multi-layered plastic container before and after the sterilization by irradiation

| Quantity of additives in polypropylene (ppm) | Before irradiation | After irradiation - dose of 25 kGy |
|---|---|---|
| IRGANOX 1010 ® (ppm) | 10 to 100 | Not detected |
| IRGAPHOS 168 ® (ppm) | 10 to 100 | Not detected |
| IRGANOX 3114 ® (ppm) | 10 to 100 | Not detected |

TABLE 10

Analysis of differential enthalpy of the outer layers of polypropylene of the bottle before and after irradiation at 25 kGy

| | Before irradiation | After irradiation - dose at 25 kGy |
|---|---|---|
| Fusion temperature (Tf ° C.) | 160.71 ± 1.53 | 159.81 ± 0.58 |
| Fusion enthalpy (ΔHf J/g) | 49.27 ± 1.90 | 49.66 ± 0.29 |

TABLE 11

Analysis of the stability of the layers by analysis of differential enthalpy of polypropylene before and after irradiation at a dose of 25 kGy and after 6 months of storage at 40° C.

| 6 months of storage at 40° C. | Product A: SUSPENSION AMOXICILLIN | Product B: SOLUTION OXYTETRACYCLINE |
|---|---|---|
| Fusion temperature (Tf ° C.) | 176.37 +/− 0.22 | 177.16 +/− 0.65 |
| Fusion enthalpy (ΔHf J/g) | 54.09 +/− 0.94 | 50.78 +/− 0.37 |

The results showed that the multi-layered plastic containers according to the present invention were not altered after sterilization by irradiation. Besides, the containers according to the present invention ensured an excellent conservation of compositions, since no interaction between the components of the layers of the container and the composition was observed after 6 months of storage at 40° C.

Example 6

Study of the Mechanical Properties of the Container

Physico-chemical properties of the multi-layered plastic bottles of 500 ml having a structure as described in the Example 4 were tested before and after sterilization by irradiation at doses of 15 kGy, 25 kGy, and 50 kGy.

Figure 4:
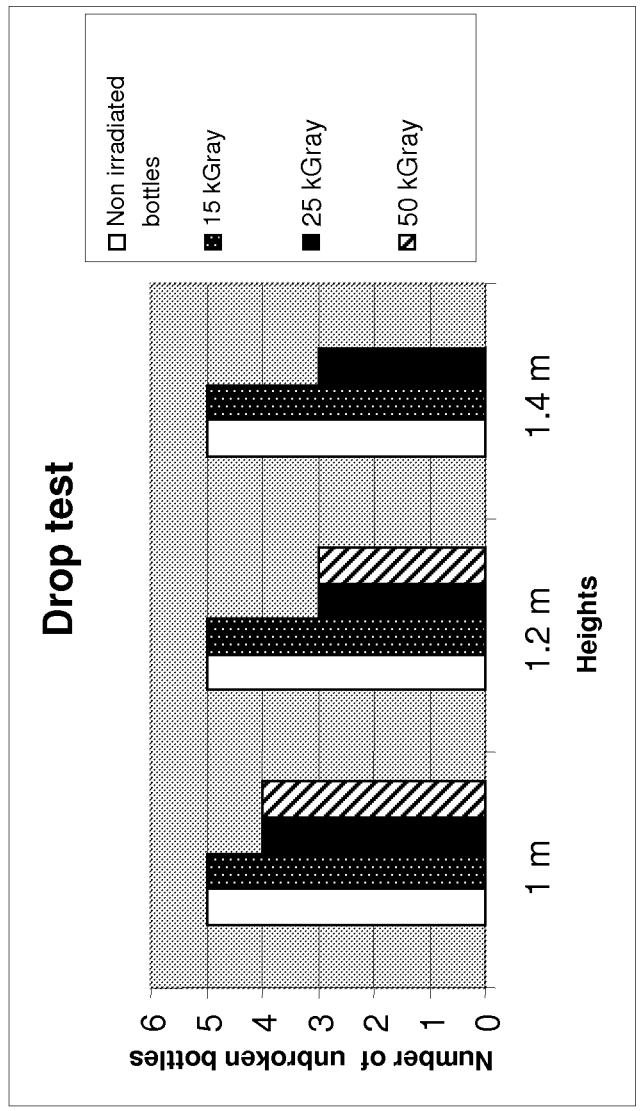
FIG. 4 shows the results of the drop test study of the container before and after irradiation at dose rates of 15 kGy, 25 kGy, and 50 kGy.

The drop test study consisted in dropping from a predefined height on a firm base a bottle filled of water. Presence of leakage evidenced brittleness or cracking of the bottle. Results as provided in FIG. 4 showed that bottles irradiated at 15 kGy stayed intact even when dropped from 1.4 m and even after irradiation.

The elasticity of the bottle was also experimented. The measure of elasticity was done using a tensile testing machine MTS Alliance RF 100. A tensile force was applied on a test tube made of plastic material (size of 80×15 mm). Mechanical properties were determined using a crosshead speed of 50 mm/min and a grip distance of 50 mm. The Young modulus was defined as a ratio of the applied force and the deformation of the test tube. Results were provided in Table 12.

TABLE 12

Calculation of the elasticity modulus or Young modulus

| | Non irradiated bottle | bottle irradiated with 15 kGy | bottle irradiated with 25 kGy | bottle irradiated with 50 kGy |
|---|---|---|---|---|
| Young modulus (Gpa) | 1.19 | 1.23 | 1.35 | 1.29 |

The Young modulus showed no statistically significant change after irradiation at doses up to 50 kGy, indicating that the rigidity of the material was not impacted by the different doses of irradiation.

Example 7

Study of the Mechanical Properties of the Container

A container (100 ml) according to the invention, as obtained by extrusion-blown molding was manufactured and comprised 5 layers, as listed in the following Table 13. The outer layer of the container contained a variable proportion of the polyoctene EXACT0203®: 0%, 10%, or 20%.

TABLE 13

| Layers | 5-layer bottle before irradiation |
| --- | --- |
| Outer layer | Polypropylene with IRGANOX 1010 ® + IRGAPHOS 168 ® + IRGANOX 3114 ® + EXACT0203 ® (0%, 10% or 20%) |
| Intermediate layer | Adhesive |
| Central layer | EVOH |
| Intermediate layer | Adhesive |
| Inner layer | Polypropylene with IRGANOX 1010 ® + IRGAPHOS 168 ® + IRGANOX 3114 ® |

Figure 7:
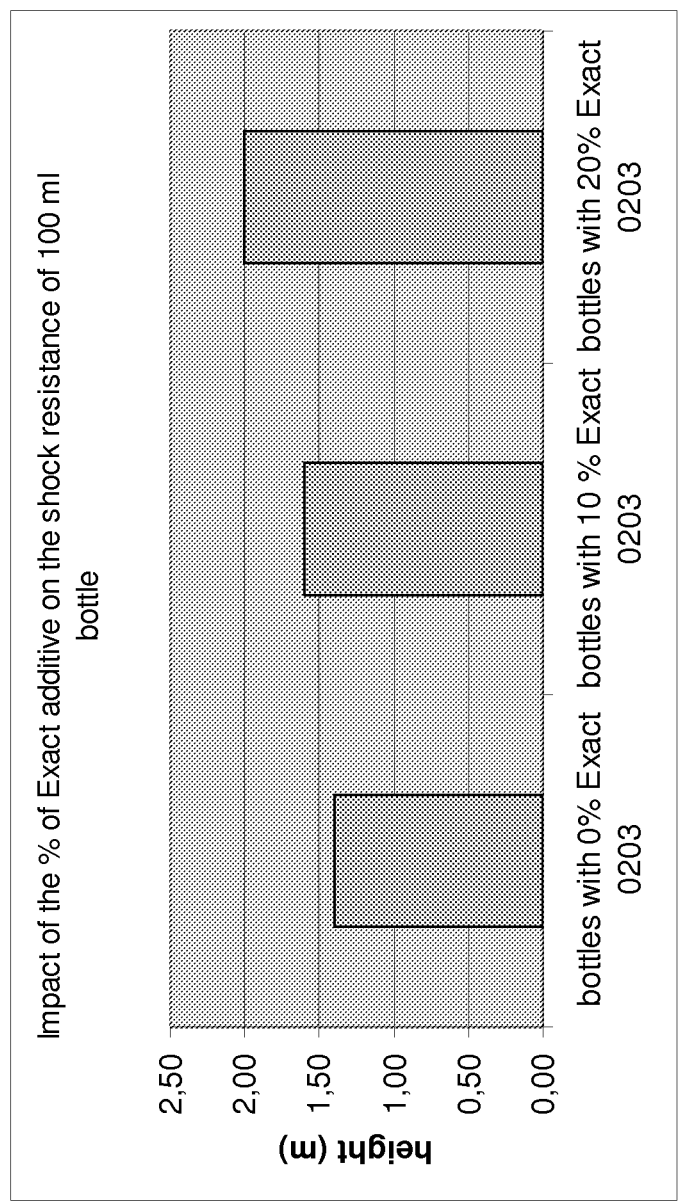
FIG. 7 shows the results of a drop test study of the container wherein the outer layer comprise 0%, 10%, or 20% of polymer EXACT0203™.

A drop test was performed to test the resistance of the multi-layers plastic polymeric containers function of percentage of EXACT0203® incorporated within the outer layer. The bottles filled with water were dropped vertically onto a metallic plaque at various heights. Results were presented in FIG. 7 showing the effect of the incorporation of polyoctene EXACT0203® on the resistance. A percentage of at least 20% of polyoctene allowed obtaining a very high resistance of the containers, even when dropped at a height of 2 m.

Example 8

Stability of the Active Substances

Figure 5:
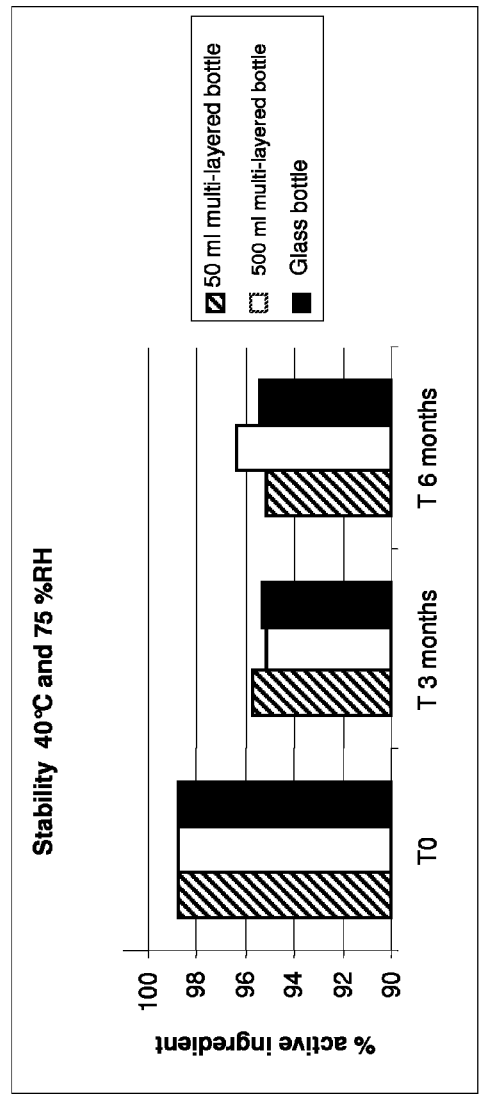
FIG. 5 shows the results of a stability study of a suspension containing 15% of an antibiotic sensitive to humidity.

A stability study was conducted on an antibiotic suspension of amoxicillin containing 15% of active ingredient very sensitive to humidity. Results were presented in FIG. 5 and evidenced that multi-layered polymeric plastic bottles guaranteed an excellent protection against humidity of the active ingredient at least for 6 months at 40° C.

Figure 6:
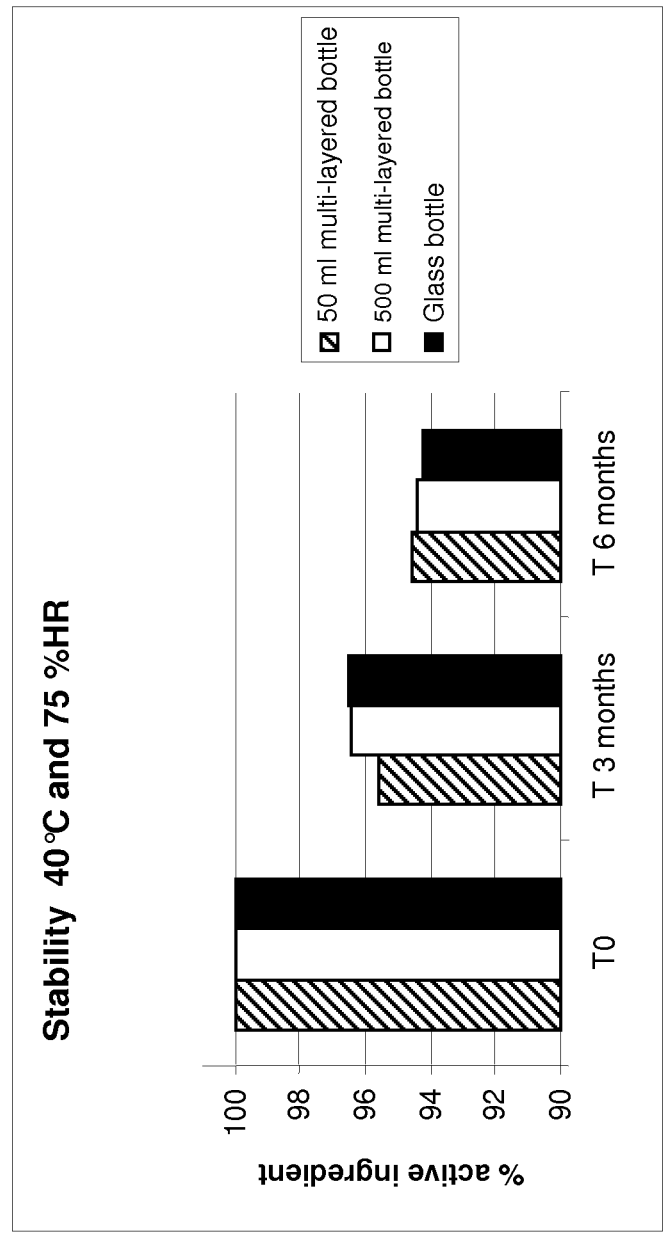
FIG. 6 shows the results of a stability study of a solution containing 10% of an antibiotic sensitive to oxidation.

Also, a stability study was conducted on antibiotic solution containing 10% tetracycline which is very sensitive against the oxidation. Results as presented in FIG. 6 evidenced that multi-layered plastic bottles guaranteed an excellent protection against the oxidation reactions of the active product at least for 6 months at 40° C.

Example 9

Stability of Composition of Ceftiofur as Stored in the Multi-Layered Plastic Polymeric Containers A stability of the oily suspension of Ceftiofur HCl 5% in the multi-layered plastic polymeric containers according to the present invention was tested. Multi-layered plastic polymeric containers were first filled with the suspensions of Ceftiofur HCl 5%, and then sterilized by irradiation. Results of the stability are provided in the following Table 14.

TABLE 14

| | Concentration of active: Ceftiofur HCl | Total Concentration of Degradation Products |
| --- | --- | --- |
| Before irradiation | 5.01% | 0.3% |
| After 15 kGy Irradiation | 5.04% | 0.3% |
| Appearance of suspension | Oily white suspension | Oily white suspension |

Example 10

Plastic Multi-Layered Containers

Figure 3:
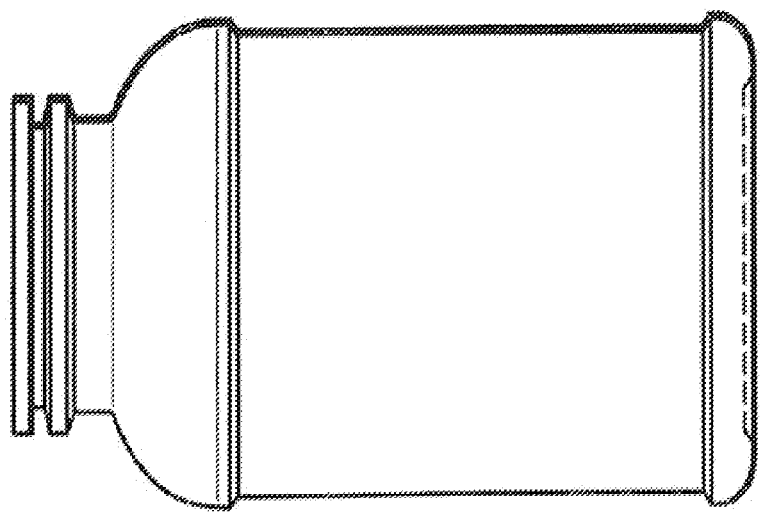
FIG. 3 displays an elevated view of a container according to the present invention.
Figure 8:
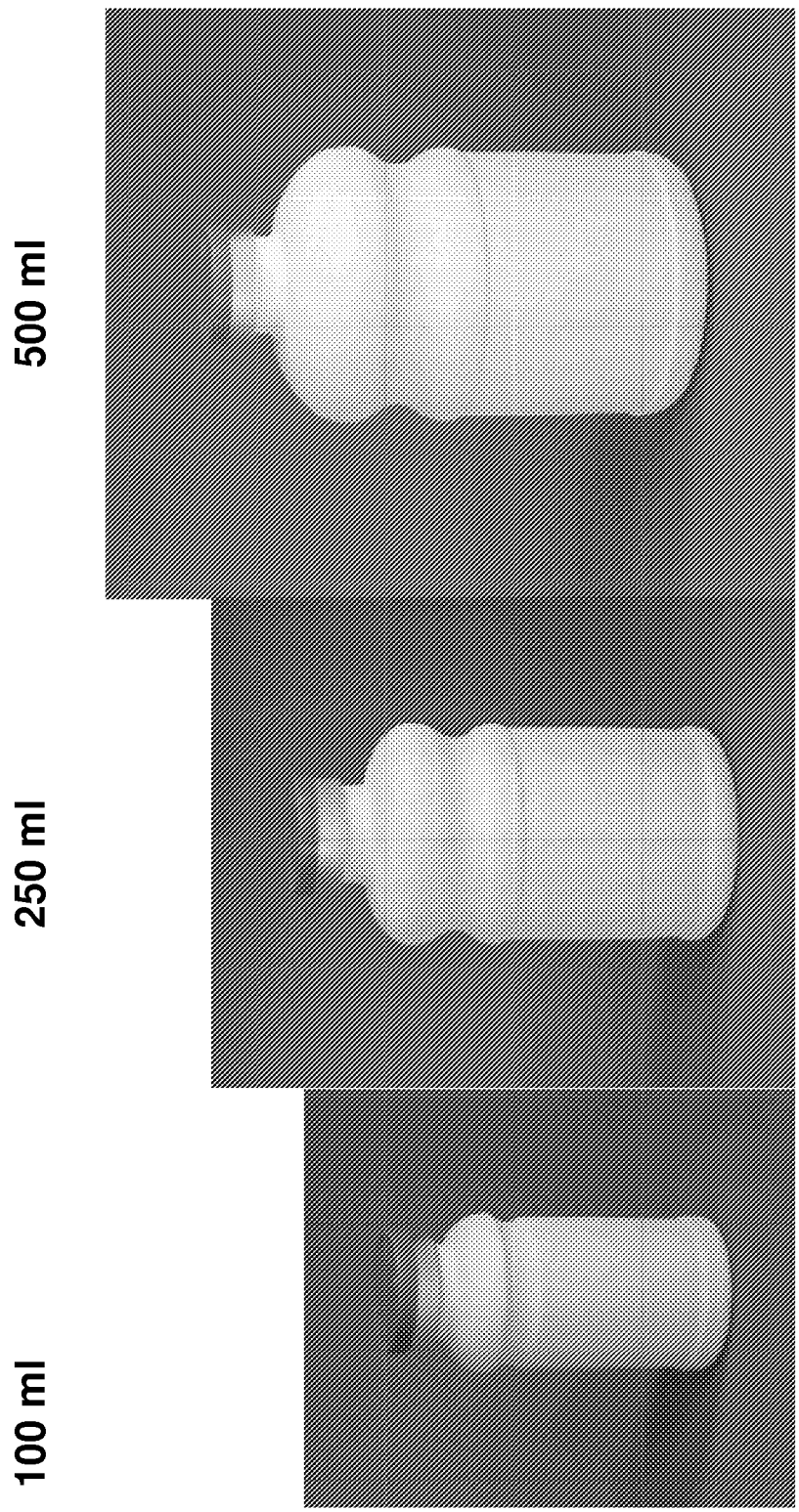
FIG. 8 displays views of container of 100 ml, 250 ml, and 500 ml according to the present invention.

Plastic multi-layered containers of various volumes for example from 50 ml to 500 ml were prepared as shown in FIGS. 3 and 8. Advantageously, the containers were shaped with a depression at the upper part allowing gripping thereof by the users. Gripping means were shown in FIG. 8 for example for the containers of 100 m, 250 ml and 500 ml without any limitations.

The invention claimed is:

1. Multi-layered plastic polymeric container in a bottle form for the storage of a composition consisting essentially of an inner polymeric layer and an outer polymeric layer in direct contact with the composition and the environment, respectively, a central gas barrier layer and two intermediate adhesive layers in between the central layer and the outer and inner polymeric layers, wherein the outer and inner layers comprise a mixture of polymers, and the outer layer comprises at least one branched polyolefin in a proportion of 5-25% by weight, relative to the total weight of the outer layer.

2. Container of claim 1, wherein the said outer and the inner layers comprise a mixture of polymers, and wherein said mixture of polymers comprises polymers chosen from polyolefins or polyesters.

3. Container of claim 2, wherein when said mixture of polymers of the outer and inner layers comprises polyolefins, said polyolefins chosen from polypropylene or polyethylene in the form of homopolymers or copolymers.

4. Container of claim 1 wherein the branched polyolefin is a polyalkene having 3 to 30 carbons.

5. Container of claim 1 wherein the branched polyolefin is a polyalkene which is present in a proportion of 20% by weight, relative to the total weight of the outer layer.

6. Container of claim 4, wherein the polyalkene is a polyoctene.

7. Container of claim 1, wherein the central gas barrier layer comprises ethylene vinyl alcohol (EVOH) or polyamide (PA).

8. Container of claim 1, wherein the outer and inner layers further comprise up to three additives chosen from antioxidants, plasticizers, stabilizers, lubricants, dyes, or mechanical strengtheners.

9. Container of claim 8, wherein the additives are antioxidants and are present within the range of up to 0.3% in the outer and inner layers by weight, relative to the total weight of each layer.

10. Container of claim 9, wherein the antioxidants are chosen from butylhydroxytoluene; ethylene bis(3,3-bis(3(1, 1-diméthyléthyl)-4-hydroxy-phényl)butanoate); pentaerythrityl tetrakis(3-(3,5-di-tert-butyl-4-hydroxy phenyl)-propionate); 4,4',4"-(2,4,6-trimethylbenzene-1,3,5-triyltrismethylene)-tris(2,6-bis(1,1-dimethyl-ethyl)phenol); octadecyl 3-(3,5-di-tert-butyl-4-hydroxyphenyl)propionate;

tris(2,4-bis(1,1-dimethylethyl)-phenyle) phosphite; 1,3,5-tris(3,5-di-tert-butyl-4-hydroxybenzyl)-s-triazine-2,4,6(1H,3H,5H)-trione; 2,2'-bis(octadecyloxy)-5,5'-spirobi(1,3,2-dioxaphosphinane); dioctadecyl disulfide; didodecyl 3,3'-thiodipropanoate; dioctadecyl 3,3'-thiodipropanoate; a mixture of components corresponding to the reaction products of di-tert-butyl phosphite with trichloride biphosphorus, with biphenyl and 2,4-bis(1,1-dimethylethyl)phenol; and copolymer of dimethyl succinate and of (4-hydroxy-2,2,6,6-tetramethylpiperidin-1-yl)ethanol.

11. Container of claim 10, wherein the outer and inner layers comprise a combination of a primary antioxidant and a secondary antioxidant, wherein each of the primary and secondary antioxidants are selected from the antioxidants listed in claim 10.

12. Container of claim 11, wherein said outer and inner layers comprise phosphite tris(2,4-bis(1,1-dimethylethyl)-phenyl) as a primary antioxidant, and pentaerythrityl tetrakis(3-(3,5-di-tert-butyl-4-hydroxy phenyl)-propionate), 4,4',4"-(2,4,6-trimethylbenzene-1,3,5-tri-yltrismethylene)-tris(2,6-bis(1,1-dimethyl-ethyl)phenol) or octadecyl 3-(3,5-di-tert-butyl-4-hydroxyphenyl)propionate as a secondary antioxidant.

13. Container of claim 12, wherein the outer layer comprises a mixture of polypropylene, polyoctene, and up to three antioxidants, wherein the inner layer comprises a mixture of polymers comprising polypropylene or polyester and up to three antioxidants.

14. Container of claim 13, wherein the outer layer comprises a mixture of polypropylene, polyoctene, and up to three antioxidants, wherein the inner layer comprises a mixture of polypropylene and up to three antioxidants, and wherein the polypropylene, the polyoctene and the antioxidants are present in sufficient amounts to allow sterilization of the container at dose rates from 15 kGy to 25 kGy without inducing any modification of physical and chemical properties of the container, or without inducing any modification of the elasticity modulus of the container as measured by the Young modulus, or allow the stable storage of a sterile non aqueous composition for at least 6 months at 40° C.

15. Container of claim 14, wherein the container consists essentially of:
an outer layer 1 comprising polypropylene, 20% of polyoctene, by weight relative to the total weight of the outer layer 1, and up to three additives chosen from pentaerythrityl tetrakis(3-(3,5-di-tert-butyl-4-hydroxy phenyl)-propionate), phosphite tris(2,4-bis(1,1-dimethylethyl)-phenyl), and 1,3,5-tris(3,5-di-tert-butyl-4-hydroxybenzyl)-s-thazine-2,4,6(1H,3H,5H)-trione;
a first intermediate adhesive layer 2 comprising an adhesive agent;
a central gas barrier layer 3 comprising of EVOH;
a second intermediate adhesive layer 4 comprising an adhesive agent; and
an inner layer 5 comprising polypropylene, and up to three additive chosen from pentaerythrityl tetrakis(3-(3,5-di-tert-butyl-4-hydroxy phenyl)-propionate), phosphite tris(2,4-bis(1,1-dimethylethyl)-phenyl) and 1,3,5-tris(3,5-di-tert-butyl-4-hydroxybenzyl)-s-thazine-2,4,6(1H,3H,5H)-trione.

16. Container of claim 15 consisting essentially of the following five layers:
an outer layer 1 in direct contact with the environment, having an average thickness ranging from 150 to 400 μm;
a first intermediate adhesive layer 2 having an average thickness ranging from 5 to 75 μm;
a central gas barrier layer 3 having an average thickness ranging from 20 to 170 μm;
a second intermediate adhesive layer 4 having an average thickness ranging from 5 to 75 μm; and
an inner layer 5 in direct contact with the composition, having an average thickness ranging from 200 to 600 μm.

17. Container of claim 14, wherein said container is sterilized by irradiation.

18. Container of claim 17, wherein said container is sterilized by gamma irradiation, before or after being filled with the composition.

19. Container of claim 4 wherein the branched polyolefin is a polyalkene having 5 to 15 carbons.

20. Container of claim 16 consisting essentially of the following five layers:
an outer layer 1 in direct contact with the environment, having an average thickness ranging from 150 to 300 μm;
a first intermediate adhesive layer 2 having an average thickness ranging from 5 to 50 μm;
a central gas barrier layer 3 having an average thickness ranging from 20 to 100 μm;
a second intermediate adhesive layer 4 having an average thickness ranging from 5 to 50 μm; and
an inner layer 5 in direct contact with the composition, having an average thickness ranging from 450 to 600 μm.

* * * * *